United States Patent
Huotilainen

(10) Patent No.: US 10,607,333 B2
(45) Date of Patent: Mar. 31, 2020

(54) REAL-TIME, FULL WEB IMAGE PROCESSING METHOD AND SYSTEM FOR WEB MANUFACTURING SUPERVISION

(71) Applicant: ABB Schweiz AG, Baden (CH)

(72) Inventor: Tommi Huotilainen, Helsinki (FI)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 16/481,896

(22) PCT Filed: Feb. 9, 2018

(86) PCT No.: PCT/EP2018/053327
§ 371 (c)(1),
(2) Date: Jul. 30, 2019

(87) PCT Pub. No.: WO2018/146271
PCT Pub. Date: Aug. 16, 2018

(65) Prior Publication Data
US 2019/0392575 A1     Dec. 26, 2019

(30) Foreign Application Priority Data

Feb. 10, 2017    (EP) .................................. 17020055

(51) Int. Cl.
*G06T 7/00*         (2017.01)
*G06T 5/20*         (2006.01)
(Continued)

(52) U.S. Cl.
CPC ........... *G06T 7/0004* (2013.01); *G01N 21/89* (2013.01); *G01N 21/8983* (2013.01); *G06T 5/20* (2013.01);
(Continued)

(58) Field of Classification Search
CPC .............................. G06T 7/0004; G01N 21/89
See application file for complete search history.

(56) References Cited

U.S. PATENT DOCUMENTS 5,113,454 A    5/1992   Marcantonio et al.
6,804,381 B2*  10/2004  Pang .................... G01N 21/898
                                                  356/238.2
(Continued)

FOREIGN PATENT DOCUMENTS

WO        2017198348 A1    11/2017

OTHER PUBLICATIONS

Kumar et al., "Defect detection in textured materials using Gabor filters", IEEE Transactions on Industry Applications, vol. 38, No. 2, Mar/Apr. 2002, pp. 425-440 (Year: 2002).*
(Continued)

*Primary Examiner* — Nay A Maung
*Assistant Examiner* — Jose Torres
(74) *Attorney, Agent, or Firm* — Whitmyer IP Group LLC

(57) ABSTRACT

A real-time, full web image processing method for analyzing formation in a web is described, the web is transported in a moving direction during a web manufacturing process, the method including the steps of acquiring a two-dimensional original image $P_0$ of the web, the image being representable as a digital image representable by a plurality of pixel values $P_{0,i,j}$ with $i \in \{1; \ldots ; I\}$, $j \in \{1; \ldots ; J\}$; and producing a plurality of P processed images $P_p$ with $p \in \{1; \ldots ; P\}$, each of the processed images being representable by pixel values $P_{p,m,n}$ with $m \in \{1; \ldots ; M\}$, $n \in \{1; \ldots ; N\}$, the processed images being obtained by spatial bandpass filtering of the original image, wherein a spatial different bandpass filter is used for obtaining each of the processed.

19 Claims, 9 Drawing Sheets

(51) Int. Cl.
*G01N 21/89* (2006.01)
*G01N 21/898* (2006.01)
(52) U.S. Cl.
CPC ............... *G06T 2207/20024* (2013.01); *G06T 2207/30124* (2013.01)

(56) References Cited

U.S. PATENT DOCUMENTS

| | | | | |
|---|---|---|---|---|
| 9,031,312 | B2* | 5/2015 | Ribnick | G01N 21/89 382/141 |
| 2002/0110269 | A1* | 8/2002 | Floeder | G01N 21/89 382/141 |
| 2004/0201669 | A1* | 10/2004 | Guha | G01N 21/89 348/126 |
| 2009/0022391 | A1 | 1/2009 | Huotilainen | |
| 2009/0060316 | A1* | 3/2009 | Ruuska | B65H 26/025 382/141 |

OTHER PUBLICATIONS

Keller, G.: "A Proposal for Standardizing online paper formation measurement", PTS News Feb. 2009. Paper Industry Magazine; pp. 16-17. 2 Pages.

Kumar A.: "Computer-Vision-Based Fabric Defect Detection: A Survey", IEEE Transactions on Industrial Electronics, IEEE Service Center, Piscataway, NJ, USA. vol. 55 Jan. 1, 2008; pp. 348-363. 16 Pages.

European Search Report Application No. EP 17 02 0055 Completed: Jul. 25, 2017; dated Aug. 2, 2017 10 pages.

Millan et al: "Flaw detection and segmentation in textile inspection", Optical and Digital Image Processing, Jan. 1, 2008; Bellingham, WA, USA; pp. 1-12. 12 Pages.

Mittal et al: "FPGA: An Efficient and Promising Platform for Real-Time Image Processing Applications", Proceedings of the National Conference on Research and Development in Hardware & Systems (CSI-RDHS), Jun. 20-21, 2008, India. 5 Pages.

International Preliminary Report on Patentability Application No. PCT/EP2018/053327 Completed: Apr. 3, 2019; dated Apr. 3, 2019 59 pages.

International Search Report and Written Opinion of the International Searching Authority Application No. PCT/EP2018/053327 Completed: Mar. 1, 2018; dated Mar. 13, 2018 16 pages.

Peifeng Zeng et al: "On-loom fabric inspection using multi-scale differentiation filtering", Conference Record of the 2002 IEEE Industry Applications Conference: 37th IAS Annual Meeting: Oct. 13-18, 2002: Pittsburgh, Pennsylvania, USA; pp. 320-326. 7 Pages.

A. Sarella: "Optimize Product Quality and Yield", Pulp & Paper International (PPI), 2009, Web Analysis. Jan. 2009 2 Pages.

* cited by examiner

REAL-TIME, FULL WEB IMAGE PROCESSING METHOD AND SYSTEM FOR WEB MANUFACTURING SUPERVISION

TECHNICAL FIELD

The invention pertains to the field of monitoring manufacturing processes. In particular, it relates to a method and a system for full web, real-time web inspection based on image processing, which is used for formation observation and analysis.

BACKGROUND

Web manufacturing refers to production and/or processing of long, thin sheets of bendable, flexible and/or soft material, in particular paper, cardboard, textile, plastic film, foil, (sheet) metal, and sometimes wire, commonly referred to as web. During production or processing, a web is generally transported over rollers in a moving direction (MD). Alternatively, the web may also be transported on some kind of conveyor belt, which may in particular be a (woven) mesh, e.g. in a so called Fourdrinier process and/or machine.

Between processing stages, webs may be stored and transported as rolls also referred to as coils, packages and doffs. A final result of web manufacturing usually comprises sheets being separated from the web by cutting or otherwise separating in a cross direction (CD) perpendicular to the moving direction. A main reason for work with webs instead of sheets is economics. Webs, being continuous, may generally be produced and/or processed at higher speeds than sheets, without start-stop issues which are inherent to production and/or processing of sheets.

For supervision and/or quality control of web manufacturing processes, web inspection systems are frequently applied which use digital imaging techniques, in particular image capture and image processing, for detecting defects or other anomalies. For web manufacturing of paper or cardboard, holes, spots and dirt particles are examples of strong defects, frequently briefly referred to as defects, whereas wrinkles, streaks and slime spots are examples of weak defects. Correspondingly, for web manufacturing of sheet metal makers, slag inclusions, cracks and scratches are examples of strong defects whereas weak cracks, weak scratches and indentations are examples of weak defects.

Defects give rise to local deviations of various characteristic image quantities, in particular of a pixel intensity level, from average and/or expected values. In the above examples, weak defects cause only a slight change in an intensity level of the digital video signal as compared to a mean variation of the intensity level measured from a faultless product. Strong defects, on the other hand, give generally rise to substantial deviations.

In addition to defect detection, supervision and/or quality control of manufacturing processes, in particular web manufacturing, may include observation, monitoring, surveying, etc. to detect a presence and/or absence, and/or a frequency, number, size, distinctness, visibility etc., of other properties, characteristics, qualities, etc. Such properties, characteristics, or qualities may include wanted and/or unwanted irregularities or unevenness of a product produced by the manufacturing processes, in particular of the web.

In particular in papermaking, formation, which may be thought of as a local non-uniformity of a sheet structure, is one such property or characteristic, and a key quality factor of the paper. Also in some other web products like for example glass fiber there are same kind of formation, i.e. non-uniform fiber clusters are causing flocs, which appear as cloudiness when one looks through the product. Also in some products there are uneven surfaces like for example coated paper with mottling, which means unwanted uneven print density and color variations. Earlier solutions for paper or surface formation floc analysis are based on off line lab measurements, snapshot, narrow band or scanning imaging methods and thus they are not capable of covering the whole web in real-time.

Formation describes how uniformly the fibers and fillers are distributed in the paper sheet. Formation is an important factor because most of the paper properties depend on it. The weakest paper properties define the end quality of paper. Bad formation causes the paper to have more weak and thin or thick areas. These affect properties like opacity and strength etc. Paper formation also affects the coating and printing characteristics of the paper. Formation problems can cause uneven dotting and mottling effect when printed. There is none standard method or unit to describe formation. It can be relative, objective or subjective evaluation.

Properties, characteristics, qualities, etc. related to formation are frequently referred to as formation features, or, in short, features.

The basic assumption behind the use of digital imaging techniques for supervision and/or quality control of web manufacturing processes is that the properties, characteristics, qualities as described above are reflected in images taken of the web or otherwise obtained. By choosing appropriate illumination and imaging setup, the defects or other properties, characteristics, qualities, etc. as described above cause intensity variations in the respective images, which in turn allow to detect their presence or absence.

Light transmission measurement or analysis can, in particular, be used for analyzing paper formation, which is often defined as variation of the mass distribution of a sheet of paper. The paper formation can be seen by holding any sheet up to the light and observing the "look through". Good formation appears uniform while bad formation has bundles of fibers causing a cloudy look. Good formation normally requires small floc sizes, which improve printability of a paper product. Several paper formation test methods have been introduced during past few decades. Most of them have been based on visible light transmission to obtain an opacity map of the sheet and then determine the histogram of gray levels of the opacity map and calculate some index of non-uniformity. Paper opacity and paper grammage are usually related but may differ depending on the light scattering properties of paper, thus based on earlier research results if more precise local grammage measurement is needed for example beta-radiation based measurement should be applied.

Another approach to describe the uniformity of formation is to analyze both the opacity variations, and the size and shape statistics of the formation flocs and/or of voids. Typically, increased floc size indicates degraded structural paper properties like cloudiness and unevenness. Large flocs can cause for example poor and uneven ink penetration. One advantage of the floc area analysis is that the measurement values are tolerant of changing lighting conditions due to, for example, environmental reasons like dirt in the imaging system, illumination non-idealities or camera optics non-idealities.

Correspondingly, optical reflection measurement or analysis, in particular, may be used for surface formation blob analysis. Unprinted paper or paperboard surface non-uniformity can be caused by, for example, surface topography variations, surface reflectance variations, and/or coating variations. And in printed products the printing quality variations can be seen as mottling, which can be defined as undesired unevenness in observed print density. All of the above mentioned reflection measurement based imaging results can also be analyzed based on methodologies corresponding to the ones used with transmission measurement.

The most traditional method of optical paper formation analysis is visual (manual) "look through" test by holding a paper against a light source. Two paper formation image examples are presented in FIG. 1. These images are based on visible light transmission measurement. Differences of the formation may clearly be seen. The left paper sample has larger flocs and more "cloudy" appearance. If one inspects the intensity histograms shown below the images in FIG. 1, one notices that the intensity histogram does not reveal the floc "cloudiness" differences of paper. This disadvantage is present in many traditional formation analysis methods.

There are also many formation analysis methods, which utilize spatial information to analyze formation. One example is the so called Kajaani index, which is based on comparison of several different size average windows, as, e.g., described in U.S. Pat. No. 5,113,454 A. The analysis based on this principle is certainly giving some valuable information about formation but the resolution and average window shapes are not optimal for real floc or blob shape analysis.

PaperPerFect method (described, e.g. in Bernié, J. P. and Karlsson, H., "Formation Guide—Measuring optical formation and applications in the paper industry", A Handbook, Second edition, Lorentzen & Wettre, 2010; or in 4. Bernié, J. P., "Measuring Formation of Paper—PaperPerFect Method—", A Handbook, Lorentzen & Wettre, 2004) and several other methods, as a further example, utilize frequency domain spectral analysis based on Fast Fourier Transform (FFT). FFT can be used to analyze periodic signals and thus measure the signal wavelengths. It is very suitable to be used for spatially stationary periodic signals like web wire or felt marking. In the case of measurement and analysis of optical formation, the FFT based analysis result does not include the floc or blob spatial location in the measurement area and it is thus possible to get the same spectral analysis results by different spatial domain images. Additionally, with FFT based analysis it is not possible to reveal and visualize an individual floc shape and analyze more precisely floc or blob morphometric properties. Also if periodic features are present, and thus some periodic signals appear, the optical formation analysis result can be dominated by the periodic signal and its harmonic components responses and the real floc size responses can be missed.

There are also some available approaches with combination of spectral analysis and spatial image analysis. Zellcheming technical sub-committee "Online sensor technology" researched this area and published a proposal for standardizing online paper formation measurement, as described in Keller, G., "A Proposal for Standardizing online paper formation measurement", PTS News 02/2009. In this case the spatial filtering is utilizing only CD and MD direction line profiles of the original image for analyzing floc sizes and orientation based on the floc size measurements in the directions of the principal axes (MD and CD). This method does not propose tools for 2D floc or blob size categorized shape analysis or formation quality change detection.

Saarela. A., "An online formation analysis function is the latest add-on to ABB's web imaging system—Optimize product quality and yield", Pulp & Paper International (PPI), 2009, introduces a formation analysis method, which utilizes fine scale spatial structure of optical formation. The structure and spatial properties of formation are not dependent on absolute intensity values, and thus the method is not sensitive to illumination changes. This method is not giving any information about formation floc or surface formation blob size categorized power and thus some valuable information is missing.

MILLAN ET AL., "Flaw detection and segmentation in textile inspection"—Optical and Digital Image Processing, 1 Jan. 2008, discusses a method to automatically segment local defects in a woven fabric that does not require any additional defect-free reference for comparison. Firstly, the structural features of the repetition pattern of the minimal weave repeat are extracted from the Fourier spectrum of the sample under inspection. The corresponding peaks are automatically identified and removed from the fabric frequency spectrum. The a set of multi-scale oriented bandpass filters are defined and adapted to the specific structure of the sample, that operate in the Fourier domain. Using the set of filters, local defects can be extracted. Finally, the filtered images obtained at different scales are inverse Fourier transformed, binarized and merged to obtain an output image where flaws are segmented from the fabric background. The method can be applied to fabrics of uniform color as well as to fabrics woven with threads of different colors.

One of the most significant disadvantages of the currently known formation analysis methods and systems is the lack of measurement coverage of the product. Most of the available optical formation analysis systems are covering only small portion of the product using offline lab imaging, web scanning, narrow band measurement area or snapshot imaging. In these cases the papermaker can miss some important process behaviors, which could be revealed by real-time full web optical formation analysis.

SUMMARY

It is thus an objective of the invention to provide a method for on-line analysis of features, in particular formation features, in a web which overcomes the disadvantages as discussed above. This objective and further objectives are solved by a method, preferably implemented on a computer, for analyzing formation features in a web, and by an optical web inspection system.

The invention comprises a method, preferably implemented on a computer, microprocessor, field-programmable gate array (FPGA) or other programmable and/or appropriately programmed data processing unit or system, for analyzing features, in particular formation features, in a web, said web preferably being transported in a moving direction during a web manufacturing process, the method comprising the steps of:

acquiring an original image $P_0$ of the web, said image being representable as a two-dimensional digital image being in turn representable by a plurality of pixel values $P_{0,i,j}$ with $i \in \{1; \ldots; I\}$, $j \in \{1; \ldots; J\}$, in particular a two-dimensional matrix having a dimension I×J; and producing a plurality of P processed images $P_p$ with $p \in \{1; \ldots; P\}$, each of said processed images being representable by pixel values $P_{p,m,n}$ with $m \in \{1; \ldots; M\}$, $n \in \{1; \ldots; N\}$, said processed images being obtained by spatial filtering, in particular spatial highpass, lowpass and/or bandpass filtering of the original image, wherein a different spatial filter, in particular spatial bandpass filter is used for obtaining each of the processed images. Instead of the notation $P_{p,m,n}$, the alternative notation $P(p,m,n)$ may also be used, i.e. $P(p,m,n)=P_{p,m,n}$ for $m\in\{1; \ldots; M\}$, $n\in\{1; \ldots; N\}$, and $p\in\{1; \ldots; P\}$.

During said web manufacturing process, a web may move in a moving direction (MD) underneath a camera. The camera may be a line scan camera, in particular video camera, which comprises a plurality of I pixel sensors arranged in a row extending in a cross direction (CD) of the web, said cross direction being perpendicular to the moving direction. In operation, the line scan camera scans the web as it passes by in order to acquire an image of said web and delivers a stream of line scans. A number J of at least partially consecutive line scans may be combined into a two-dimensional digital image of a section of the web in moving direction, said digital image having a pixel dimension of I×J pixels and comprising a plurality $P=I\cdot J$ pixels $P_i$ with $i\in\{1; \ldots; I\cdot J\}$, each pixel having one or more pixel values representative of a local color or total intensity, hue, saturation. In particular, the digital image may be representable by a plurality of pixel values $P_{0,i,j}$ with $i\in\{1; \ldots; I\}$, $j\in\{1; \ldots; J\}$, where preferably $I,J>100$, most preferably $I>1000$ and/or $J>1000$ may hold. The pixel values may have a certain bit depth or bit resolution, and may in particular be binary values representable by a single bit, which bit depth may correspond to a bit depth of the line scan camera, or have been obtained through up- or downsampling of the bit depth. For a line scan rate $f_{line}$, and a transport velocity $v_{MD}$ of the web in moving direction, a length of the section of the web in moving direction imaged this way is $Y\cdot v_{MD}/f_{line}$. The digital image may, in particular, be a grayscale or black-and-white, in particular binary, image; and may, alternatively be obtained by a still camera, by conversion from an analogue still or video image, etc. An area of the web imaged by the digital image may, at least approximately, correspond to the at least almost the whole web. In particular, for characteristic dimensions of the web. In particular, for a width $w_{web}$ of the web in cross direction, a characteristic dimension of the imaged area $d_{spot}$, in particular a first width in CD, a first length in MD and/or a first diameter, may satisfy $d_{spot}>0.3\ w_{web}$, preferably $d_{spot}>0.6\ w_{web}$, and most preferably $d_{spot}\approx w_{web}$. Preferably, both first length and first width are larger than $0.3\ w_{web}$ or $0.6\ w_{web}$, and most preferably at least approximately equal $w_{web}$.

While the digital image of the web thus acquired may be stored, in particular in a memory of a computer, in particular a standard computer, or a graphics processing unit, and the method in accordance with the invention be carried out on the stored digital image, in particular by an image processing program or application being executed on or by the computer, this is preferably not being done for various reasons related to efficiency.

Preferably, the method in accordance with the present invention is carried out on image data being streamed from the line scan camera, preferably in a single-pass algorithm, wherein each pixel or each group of pixels is processed only once. In other words, once a particular pixel or pixel group has been processed, there is no possibility of going or referring back to that particular pixel or pixel group. Thus, at each point in time, only a partial image of the web, i.e. a digital image of a portion of the web having a characteristic dimension $d_{partial}$, in particular a second width in CD, a second length in MD and/or a second diameter, may satisfy $d_{partial} \ll w_{web}$, preferably $100\ d_{partial} \ll w_{web}$. In particular, if the first length as described above is given by $I_1$ and said second length by $I_2$, $I_2 \ll I_1$ may hold, preferably $100\ I_2 \ll I_1$.

Formation analysis is preferably based on product imaging by utilizing appropriate illumination, imaging configuration, optics and camera. Careful imaging configuration with illumination dynamics control is preferable to ensure that all the relevant information is available e.g. in raw video signal for different kinds of analysis purposes. The optical formation analysis method may preferably use the same, preferably corrected, video source as other transmission measurement based web inspection methods or reflection measurement based web surface inspection methods that have been or will be applied to the web. Before the actual formation analysis, the generated raw image data may be analyzed by imaging hard-, firm-, and/or software, which may first make several corrections to incoming raw data, for example position-dependent brightness corrections and/or gray-scale transformations. Appropriate flat field correction and/or imaging dynamics control are preferably applied for reliable web imaging and thus for optical formation analysis as well. Video correction may preferably be used to correct the raw video signal to have zero mean and linear illumination response. In this context, linear may mean that when, e.g., a transparent target object is illuminated with a transmission light source the intensity response after gain correction has same level even with changing illumination conditions. Image and/or video correction as described above may thus improve the quality of, e.g., formation floc or blob analysis based on intensity and/or contrast measurements.

The first stage of optical formation analysis and measurement may thus include image, in particular video signal, corrections including: configuration of the system to have linear response, dynamic range optimization, and/or flat field correction to normalize the image to have the mean for example in the middle of the image dynamic range. Normally, by the flat field correction method the raw video input signal is corrected to have the average background intensity level in the middle of the whole dynamic range. Problems that may arise due to non-uniform or (time-) varying illumination conditions, in particular related to an illumination level; and otherwise lead to the same target object like a formation floc causing variable absolute intensity response in the raw video signal, may thus be eliminated. A corrected image may preferably also be provided as a stream, in particular in the form of a corrected video signal.

A plurality of P processed images $P_p$ with $p\in\{1; \ldots; P\}$ is subsequently produced from the digital image, in particular from the digital image representing an original or corrected image, wherein preferably $P>4$, $P\geq 8$, or, most preferably $P\geq 16$ is fulfilled. Each of said processed images $P_p$ is obtained by spatial filtering, in particular spatial bandpass filtering of the original image, and may in turn be represented by pixel values $P_{p,m,n}$ with $m\in\{1; \ldots; M\}$, $n\in\{1; \ldots; N\}$. The dimensions of the processed images may, in particular, correspond to the dimensions of the two-dimensional digital image representing the original image, in particular the original image itself, i.e. $I=M$ and/or $J=N$. Alternatively, $I>M$ and/or $J>N$ may hold, where, in particular I and/or J man be an integral multiple of M and N, respectively. A different spatial filter, in particular spatial bandpass filter, $F_p$ is used for obtaining each of the processed images, i.e. any two images $P_{p1}$ and $P_{p2}$ with $p1\neq p2 \in \{1; \ldots; P\}$ are obtained by using different filters $F_{p1}$ and $F_{p2}$. Preferably, bandpass filters $F_p$ with $p\in\{1; \ldots; P\}$ are chosen to at least essentially segment a spectrum of spatial frequencies contained in the original image, preferably into subranges adjacent to one another. In particular, this may be achieved by selecting an upper cut-off frequency $f_{max,p}$ of a first spatial bandpass filter $F_p$ to at least essentially match a lower cut-off frequency $f_{min,p+1}$ of a second spatial bandpass filter $F_{p+1}$, i.e. to select $f_{max,p} \approx f_{min,p+1}$ for $p \in \{1; \ldots; P-1\}$.

In particular for such a selection of spatial bandpass filters, p may be thought of as in indication for, in particular as an index indicating, a size category, size class or scale $S_p$, wherein $p \in \{1; \ldots; P\}$. The pixel values $P_{p,m,n}$ correspond to floc or blob power in size category $S_p$ at the respective pixel location m,n.

Characteristics or behavior of the different filters may be adaptable, and/or allow for fine tuning. This may in particular be done by adapting and/or setting values for one or more filter parameters for some of the filters or for each filter.

If the method in accordance with the present invention is carried out on image data being streamed from the line scan camera as described above, the pixel values $P_{p,m,n}$ may be obtained successively, in particular by applying one or more of the filters successively to individual pixels or subsets of pixels corresponding to the original or corrected image on the fly and/or in real-time, i.e. while they are being streamed and without waiting for subsequent pixel data to arrive.

This, in turn, allows for using, in particular taking into account, at least some pixel values $P_{p,m0,n0}$ which have already been received to adapt characteristics of at least one of the different filters prior to receiving further pixel values $P_{p,m,n}$ with $m \neq m0$ and $n \neq n0$. Said pixel values $P_{p,m,n}$ may be regarded as components of a feature vector, in particular a local feature vector as will be described in more detail below. Thus, said local feature vector may be used for adapting filter parameters. In particular, already obtained local feature vectors or local feature vector parameters from a neighborhood of a pixel or pixels to which filtering is to be applied may be considered in adapting filter parameters. In particular, filter characteristics used for obtaining $P_{p,m,n}$ may take into account $P_{p,m0,n0}$ with $m \neq m0$ and $n \neq n0$ as described above, and further with $m \approx m0$ and $n \approx n0$; and preferably $m > m0$ and $n > n0$ (where it may be assumed that m and n increase, at least in general, monotonically during streaming).

The plurality of processed images as described above may be obtained subsequently, with the individual filters $F_p$ applied subsequently. Preferably, some or all of the individual filters $F_p$ applied in parallel, in particular by using an FGPA adapted for parallel operation, wherein an input signal, in particular a streamed video signal, is delivered to several, preferably all, filters $F_p$ at the same time, in particular, within one clock cycle. The results of the different filters are then available simultaneously and/or in parallel; in particular, the plurality of processed images are obtained as parallel video streams, and may thus be thought of as signals containing or representing the pixel values $P_{p,m,n}$, and/or of feature signals for each scale $S_p$.

In particular, as a next stage of the optical paper formation or surface formation analysis spatial digital filtering may be applied to corrected image or video signal to emphasize, isolate, or otherwise enhance the different size formation structures. Spatial 2D lowpass, bandpass and highpass filtering may be used to separate formation features of different sizes, and then analyze and visualize the formation features.

The method for analyzing formation in a web as described above allows for on-line, full web analysis in real time. Nevertheless, the method may also be applied to subareas or subregions of the web. This may either be done by imaging subareas or subregions only, as for example in combination with CD band measurement, where only a section of the web in CD is imaged, where only part of the cross direction is imaged, or scanning imaging, where such a section moves back and forth in CD across the web. Alternatively, it may be achieved by using only a subset of the pixels provided by the camera when acquiring the image as described above. The processed images as obtained by spatial bandpass filtering of the original image allow for analyzing formation quality with respect to a plurality of size categories corresponding to the respective bandpass filter properties. Spatial information related to formation quality is retained, in particular if M=I and N=J is chosen, thus allowing for features obtained or observed as part of the formation to be located on the web, so that appropriate measures may be taken if desired.

In a preferred variant of the method in accordance with the invention, the method further comprises the step of combining at least two, preferably all, of the processed images $P_p$ with $p \in \{1; \ldots; P\}$ to obtain a feature map F being representable by values $F_{m',n'}$ with $m' \in \{1; \ldots; M'\}$, $n' \in \{1; \ldots; N'\}$, preferably $m' \in \{1; \ldots; M\}$, $n' \in \{1; \ldots; N\}$, which values represent pixels of the feature map.

The feature map allows e.g. for concise and/or enhanced visualization of formation and formation analysis results. In particular, each pixel of the feature map may represent one component of a local feature vector corresponding to said pixel; wherein different pixels may represent different components, which may be selected according to various schemes as exemplary described below.

In particular, the feature map $F_{m',n'}$ may be obtained according to $F_{m',n'} \stackrel{def}{=} P_{max,m',n'}$ with $P_{max,m',n'} = \max\{P_{p,m',n'} | p \in \{1; \ldots; P\}\}$.

The feature map, in particular, provide information as to formation features of which size category or size class are most prominent for different regions/subareas of the web. A size category or size class may also be referred to in short as a scale.

More specifically, the feature map $F_{m',n'}$ may preferably be obtained according to $F_{m',n'} = F(m',n') \stackrel{def}{=} p_{max, m',n'}$ with $P(p_{max,m',n'}, m',n') > P(p,m',n')$ with $p \in \{1; \ldots; P\} \backslash \{p_{max,m',n'}\}$. $F_{m',n'}$ may then be thought of as an index value corresponding to an index $p_{max,m',n'}$ of a predominant size category for m',n'. The feature map may in particular be presented and/or displayed as a color or grayscale image composed by pixels, wherein the pixel values are given by $F_{m',n'}$. Each color or grayscale does then correspond to a predominant size category.

In particular, if M'=M=I and N'=N=J are chosen, location information related to such formation features is contained at a spatial resolution identical to a spatial resolution of the original image; and color and/or grayscale images of the feature map indicate the predominant size category at each pixel location of the two-dimensional digital image by which the original image may be represented.

The term feature, in this context, may refer to formation features as described above including various aspects of or irregularities in formation. In particular, the term may refer to items as floc, blobs, voids. The term may also refer to properties, characteristics, qualities, etc. of items as, in particular strong or weak, defects. The term may refer to a presence, absence or frequency of occurrence of such items; shape, orientation, distinctness, visibility, transmissivity, reflectivity, etc. of such items, etc.

The feature map F may preferably be displayed as a two-dimensional digital color image, with a different color being displayed for each different value of $F_{m',n'}$ with $m \in \{1; \ldots; M'\}$, $n \in \{1; \ldots; N'\}$. More preferably, an enlarged subsection of the feature map may be displayed.

The feature map as described above is a scalar feature map, representable by scalar values $F_{m',n'}$ with $m' \in \{1; \ldots; M'\}$, $n' \in \{1; \ldots; N'\}$. Similarly, a vector feature map, representable by vector values $F_{m',n'}$ with $m' \in \{1; \ldots; M'\}$, $n' \in \{1; \ldots; N'\}$ may be established or derived. For example, a first component of $F_{m',n'}$ may contain values $P_{max,m',n'}$ as described above, while a second component may contain values $P_{min,m',n'}$ with $P_{min,m',n'} = \min\{P_{p,m',n'} | p \in \{1; \ldots; P\}\}$.

In a preferred variant of the method in accordance with the invention, the processed images $P_p$ with $p \in \{1; \ldots; P\}$ are thresholded, in particular converted to binary images representable by pixel values $P_{p,m,n} \in \{0; 1\}$ for $p \in \{1; \ldots; P\}$, $m \in \{1; \ldots; M\}$, $n \in \{1; \ldots; N\}$.

By applying appropriate thresholding, areas of the processed images where no features are present, or where features are normal, unobtrusive, or within acceptable levels from a quality control point of view, may, e.g. have maximum or minimum pixel value, and, in particular, appear as black or white regions, respectively, in a standard grayscale representation of the processed images.

In a preferred variant of the method in accordance with the invention, the method further comprises the step of: determining, from the processed images $P_p$ with $p \in \{1; \ldots; P\}$, a feature vector, in particular an image feature vector $v = (v_1, \ldots, v_{P'})$, preferably with $P' \leq P$, most preferably with $P' = P$, wherein vector component $v_p$ of said image feature vector $v$ may, in particular, be determined from one or more of the processed images, preferably from processed image $P_p$.

The components $v_p$ of the image feature vector may, in particular, serve as a quantitative indication or measure of a presence—or absence—of one or more of features as detailed above in a respective size class $S_p$ with $p \in \{1; \ldots; P\}$, where said size class may correspond to or be defined by the spatial frequencies contained in the pass range of bandpass filter $F_p$. The components $v_p$ of the image feature vector may in particular represent a maximum, minimum or average intensity of the corresponding processed image $P_p$, a pixel count representative of a number of pixels having a pixel value above or below a predetermined threshold, etc. In particular, when the processed images are binary images, the components $v_p$ of the image feature vector may in particular represent the number of pixels having a pixel value of zero, or the number of pixels having a pixel value of one. When applied to floc or blob analysis, the components $v_p$ of the image feature vector may then be regarded as a measure of floc or blob power, corresponding to an area of floc or blob weighted by intensity.

Alternatively, an area of floc or blob weighted by one, corresponding to area only, may be used for floc or blob analysis.

For the case described further above where the dimensions of the two-dimensional digital image representing the original image, in particular the original image itself, correspond to the dimensions of the processed images $P_p$, i.e. I=M and J=N, a local feature vector is obtained for every pixel of the digital image.

Both local and image feature vector $v$ may also contain more than P components, $P'>P$, where additional components may be obtained from other image processing methods, which may in particular be carried out simultaneously and/or in parallel with the method as described herein.

Preferably, the image feature vector $v$ is determined in real time. If the original image is obtained by a video camera, the image feature vector $v$ may be updated whenever the video image is updated, and/or when a video signal changes. In particular, when the original image is acquired or otherwise obtained from image data being streamed from a video camera, in particular a line scan camera, the image feature vector is preferably updated concurrently with the arrival of new streaming data blocks, units, etc.

If the image feature vector $v$ is determined in real time and updated as described above, the vector, and, in particular the vector components may then be thought of as a time-dependent or time varying signals, in particular feature signals, or in other words as signals that may be represented as a function of time t. Such signals may be particularly helpful for online monitoring of formation quality.

The method in accordance with the invention preferably includes also a mechanism to calculate a gain corrected reference signal, which can preferably be used for monitoring changes in the formation. Preferably, is also possible to set alarming threshold levels. The gain corrected reference signal can include, in particular, both the floc or blob size data and the shape analysis results.

The gain corrected reference signal may in particular be obtained by means of a correction method, in which a gain value is stored in memory for every signal. So for example for a number P of image feature vector components $v_p$ with $p \in \{1; \ldots; P\}$ a corresponding number of feature signal gain values g(p) are adjusted regularly by operator defined rate, e.g. at every clock cycle, or for every new pixel being streamed. Thus, a corrected feature signal $f_{corr}(p)$ is given by $f_{corr}(p) = v_p g(p)$, where g(p) is adjustable gain, $v_p$ may be thought to of as a raw feature signal $f_{raw}(p)$, and p may be regarded as an order number of the signal value. Preferably, in the correction method, a target for signal values in long-term is in the middle of an entire dynamic range of the feature signal. If the corrected feature signal $f_{corr}(p)$ value is above the target the gain value may be reduced. Correspondingly, if the signal value is below the target the gain value may enlarged. Hence, the adjusting method can be expressed by $g_{new}(p) = g_{old}(p) + \text{sign}(f_{target} - \text{nagc}(p)) \text{rate}$ where sign is a function which returns 1 for positive and −1 for negative arguments, rate defines the speed of adjusting (feature signal correction adjust rate control parameter) and $f_{target}$ is the target value.

The gain corrected reference signal allows for easy, reliable and quick detection of formation quality changes. In particular, a graphical representation of the image feature vector may preferably be displayed, e.g. in form of a bar graph, to facilitate real-time monitoring of the web production process. Graphical representation of the image feature vector may preferably be displayed together with the feature map to allow for even more reliable monitoring. Alternatively, a length |v| of the image feature vector, where |•| is an appropriate metric defined on a vector space containing v may be monitored and/or displayed, and may, in particular, serve as an observable, and or as a controlled quantity of a control loop.

Preferably, two or more different feature maps and/or image feature vectors are produced simultaneously for different subregions or subareas of the web, preferably in real time. In particular, a first, global, image feature vector $v_1$ may be determined on the basis of at least essentially the whole original image, and a second, local, image feature vector $v_2$, and or a feature map F, may be determined on the basis of a subregion or subarea of the original image. By comparing the first and second feature vectors, an indication of local deviation of local properties, characteristics, qualities, etc. from their global counterparts may easily be detected. This may in particular be effected by determining a distance $|v_1-v_2|$ between the vectors, where $|\cdot|$ is an appropriate metric defined on a vector space $v_1$ and $v_2$ belong to.

In a preferred variant of the method in accordance with the invention a plurality of smoothed images $B_q$ with $q \in \{1; \ldots; Q\}$ each of said smoothed images being representable by pixel values $B_{q,m,n}$, with $m \in \{1; \ldots; M\}$, $n \in \{1; \ldots; N\}$, is produced in a first step, each of said smoothed images being obtained applying a spatial low pass or smoothing filter to the original image, with a different filter being used for each of the smoothed images $B_{q,m,n}$; and each of the processed images $P_p$ with $p \in \{1; \ldots; P\}$ is subsequently produced by subtracting two smoothed images $B_{p1,m,n}$, $B_{p2,m,n}$ with $p1 \neq p2$.

In particular, spatial bandpass filter may be designed by utilizing the difference of two spatial lowpass, e.g. smoothing filters, which have different width. Difference of Gaussians (DoG) is a well-known example of a filtering method, which is based on the subtraction of two Gaussian lowpass filtered images [xx]. These two blurring Gaussian filter kernels have different width. As a result one will get a bandpass filter, which preserves spatial information that exist between the cut-off frequencies of the two lowpass filters. One important application area of DoG method is blob detection, which can be achieved by utilizing DoG filter bank. The magnitude of the bandpass filter response will achieve a maximum at the center of the floc or blob and the corresponding filter, which provides the maximum, will also define the floc or blob size. In this way, when applying the bandpass, in particular DoG, method to formation image, it is possible to analyze the size categorized power of the individual paper formation flocs or surface blobs. Each spatial bandpass filter result also represents the specific size category formation flocs or surface formation blobs and it is possible to analyze not only the "power" of floc or blob, but also more precise floc or blob shape and spatial distribution with correct localization. All of these bandpass filtering results may also be visualized, which can be a valuable feature to monitor paper making process behavior.

One method enhancing feature is to use different spatial filter or smoothing window sizes in cross and machine directions. This gives options to analyze or detect some specific elongated floc or blob behaviors.

More specifically, by using different widths (different coefficients) for the bandpass filter CD and MD directions (and also diagonal filters can be designed) it's possible to tune this new formation method and to analyse and detect the quality of different kinds of textures in or on a web product, for example for paper watermark analysis and detection.

Similar analysis methods can be applied to the void areas of the paper formation or light areas of the surface formation.

With the method in accordance with the invention and its variants as described above, real-time smart camera based web inspection systems can utilize all the video data and achieve paper property measurement coverage of the whole web. The real-time analysis of the paper formation flocs or surface formation blobs can consist of geometric methods like measurement of size, lengths, widths, angles and ratios connected with: 1. intensity based methods like intensity average measurement, and 2. spatial size distribution measurements. All of these methods must run in real-time simultaneously with the other web inspection functions like for example detection and analysis of paper or paperboard defects.

This allows for pulp, paper, and paperboard web imaging systems to handle various different image analysis tasks and support higher resolutions and dynamic ranges in real-time. One preferred approach for facilitating the challenge caused by the enormous increase in the amount of image data is to use a smart field-programmable gate array (FPGA) based imaging camera which processes the incoming raw image data, and transfers only the results and target images having the desired resolution and dynamic range, as e.g. described in Mittal, S., Gupta, S., and Dasgupta, S., "FPGA: An Efficient And Promising Platform For Real-Time Image Processing Applications", Proceedings of the National Conference on Research and Development in Hardware & Systems (CSI-RDHS), 2008. In this way it is possible to reach real-time processing performance for the full web, utilizing all of the available web data for product analysis, yet still reduce the amount of report data FPGA based hardware platforms also make it possible to provide new measurement features for new challenges, upgrade existing systems with these new features, and thus also extend the life cycle of web imaging systems.

The method in accordance with the invention and its preferred variant, thus allow pulp or paper manufacturers to: (1) monitor the overall quality factors of a product online, (2) react immediately to improve the product manufacturing process, (3) evaluate the overall product quality, and (4) classify the manufactured product areas based on specific customer requirements. This means huge savings compared to cases where a partial measurement result is used for downgrading the product quality causing significant amounts of good quality product to be downgraded as well.

The method and system in accordance with the invention is applicable also for many other "mass" production environments based on some moving conveyor belt, for example food industry: fish feed, animal food, flour, cereals, etc.; and to related analysis methods.

The present disclosure also includes embodiments with any combination of features which are mentioned or shown above and/or below, in various embodiments or variants. It also includes individual features as shown in the Figures, even if they are shown there in connection with other features and/or are not mentioned above or below. The disclosure comprises embodiments which exclusively comprise the features described in the claims or the exemplary embodiments, as well as those which comprise additional other features.

The above and other aspects of the invention will become apparent from and elucidated with reference to the embodiments described hereinafter.

BRIEF DESCRIPTION OF THE DRAWINGS

The subject matter of the invention will be explained in more detail in the following text with reference to exemplary embodiments which are illustrated in the attached drawings, of which.

DETAILED DESCRIPTION

Figure 2:
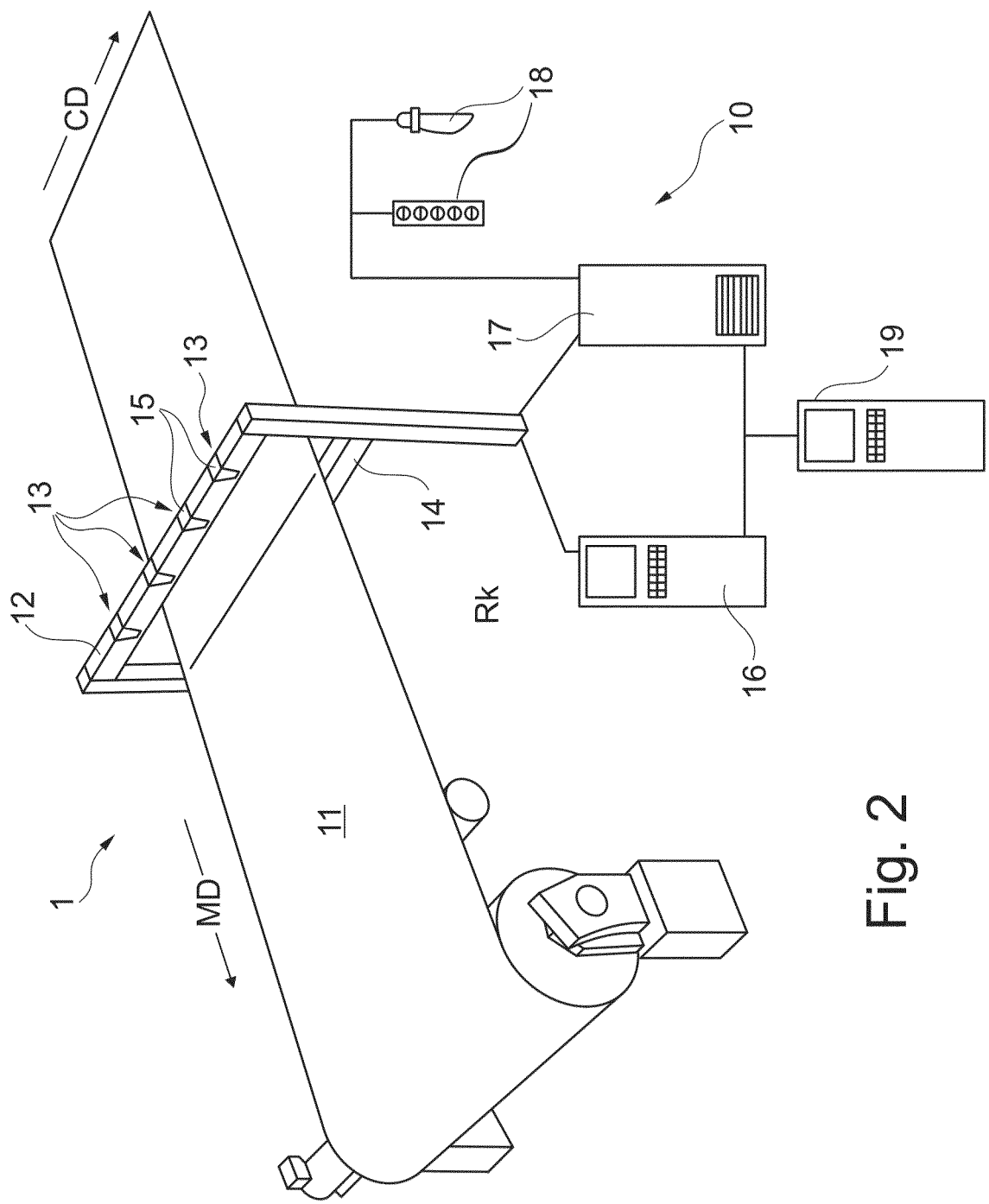
FIG. 2 illustrates a web inspection system which may be used for applying the method in accordance with the present invention to a web manufacturing process.

FIG. 2 illustrates a web inspection system which may be used for applying the method in accordance with the invention to a web manufacturing process.

During said web manufacturing process, a web 11 moves in a moving direction MD underneath a line scan camera 12, preferably a CMOS line scan camera, which comprises a plurality of X pixel sensors 13 (of which only four are shown for clarity) arranged in a row extending in a cross direction CD of the web perpendicular to the moving direction. In operation, the line scan camera 12 scans the web as it passes by in order to acquire an image of said web and delivers a stream of line scans. A number Y of consecutive line scans may be combined into a two-dimensional digital image of a section of the web in moving direction, said digital image having a pixel dimension of X·Y pixels and comprising a plurality P=X·Y pixels $P_i$ with $i \in \{1; \ldots; X \cdot Y\}$, each pixel having one or more pixel values representative of a local color or total intensity, hue, saturation. The pixel values may have a certain bit depth or bit resolution, and may in particular be binary values representable by a single bit, which bit depth may correspond to a bit depth of the line scan camera, or have been obtained through up- or down-sampling of the bit depth. For a line scan rate $f_{line}$, and a transport velocity $v_{MD}$ of the web in moving direction, a length of the section of the web in moving direction imaged this way is $Y \cdot v_{MD} / f_{line}$.

In the exemplary setting of FIG. 2, line scan camera 12 has 4000×1 pixels, and is capable of scanning 80.000 lines per second. Thus, X=4000 may in particular be chosen as pixel resolution in CD.

Line scan camera 12 can be directly or indirectly coupled to image-processing unit 15. Functions of the image-processing unit 15 may also be integrated with the camera, in which case the camera is a more complicated and self-contained image-processing unit. Image data output of an analog camera, for example an analog CCD or CMOS line scan camera or matrix camera, has to first be converted to digital format. Digital camera output is typically more ready for digital processing in the image-processing unit 15. The image-processing unit 15 receives from the line scan cameras 12 a digital representation of the view imaged by said cameras. The representation is in the form of a series of digital numbers. Image processing unit 15 interprets this data as an electronic image, which is elsewhere referred to as an image, on the basis of the information it has about the properties of the Line scan camera 12.

The signal from the line scan camera 12 is forwarded to the next processing step, which is image analysis. This step can be done in image-processing unit 15 or in a separate computer, which may be a part of an operator station 16 of the visual inspection system 10 and it is typically common to all the cameras 13. Image analysis comprises, for example, further segmentation of the interesting areas, such as defects, in the image. After segmentation, features describing properties of the regions found by segmentation can be extracted. The features are numeric values that will be used in recognizing the areas, i.e. in classifying them.

Figure 1:
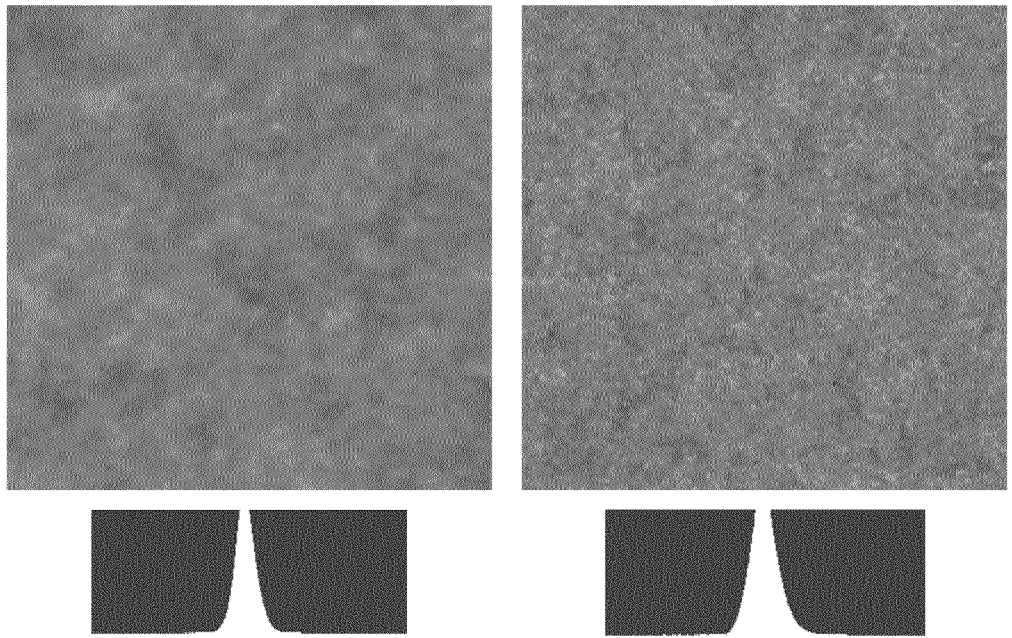
FIG. 1 shows exemplary images of two paper types having different formation.

The image-processing unit 15 is a separate, typically programmable, hardware unit. It can be partially or totally integrated with the line scan camera 12, as depicted in FIG. 1. It can be also a personal computer or any other type of universal computer. One computer may take care of image data processing of one or several cameras. The method for processing image data is applied in this stage. The detection, i.e. obtaining an inspection signal that is recognized coming from a defect, is performed and by means of the method for processing image data the image of the web is divided into interesting regions. The outcome of this processing stage is a set of electronic images representing segmented parts of the web, the images being manipulated electronically to meet requirements of the application at hand.

Operator station 16 contains the user interface of the visual inspection system 10. It is used for entering various tuning parameters and selecting desired displays and reports, which for example show the status of the system and the quality of the inspected products. Naturally the visual inspection system 10 requires separate means for supplying power to the system and devices for interfacing with the external systems such as the process itself. These means, which are well known to those of ordinary skill in the art, can be located in an electronic cabinet 17. In addition to operator station 16, external devices 18 can be used for alerting the operator.

The image data may be stored in an image database. The image collection of the database consists of different types of digitized web defects. In addition to formation analysis, defects may be detected and their images are digitized from a running web. For classifying the defects a classifier 19 may be used. Defect classification may, in particular be based on the method as described in EP patent application EP 16180281.4, which is hereby included by reference in its entirety; or in Huotilainen, T., Laster, M., Riikonen, S., "Real-time ROI Morphometrics in High Quality Web Imaging", PaperCon, 2016, which is hereby included by reference in its entirety.

Figure 3:
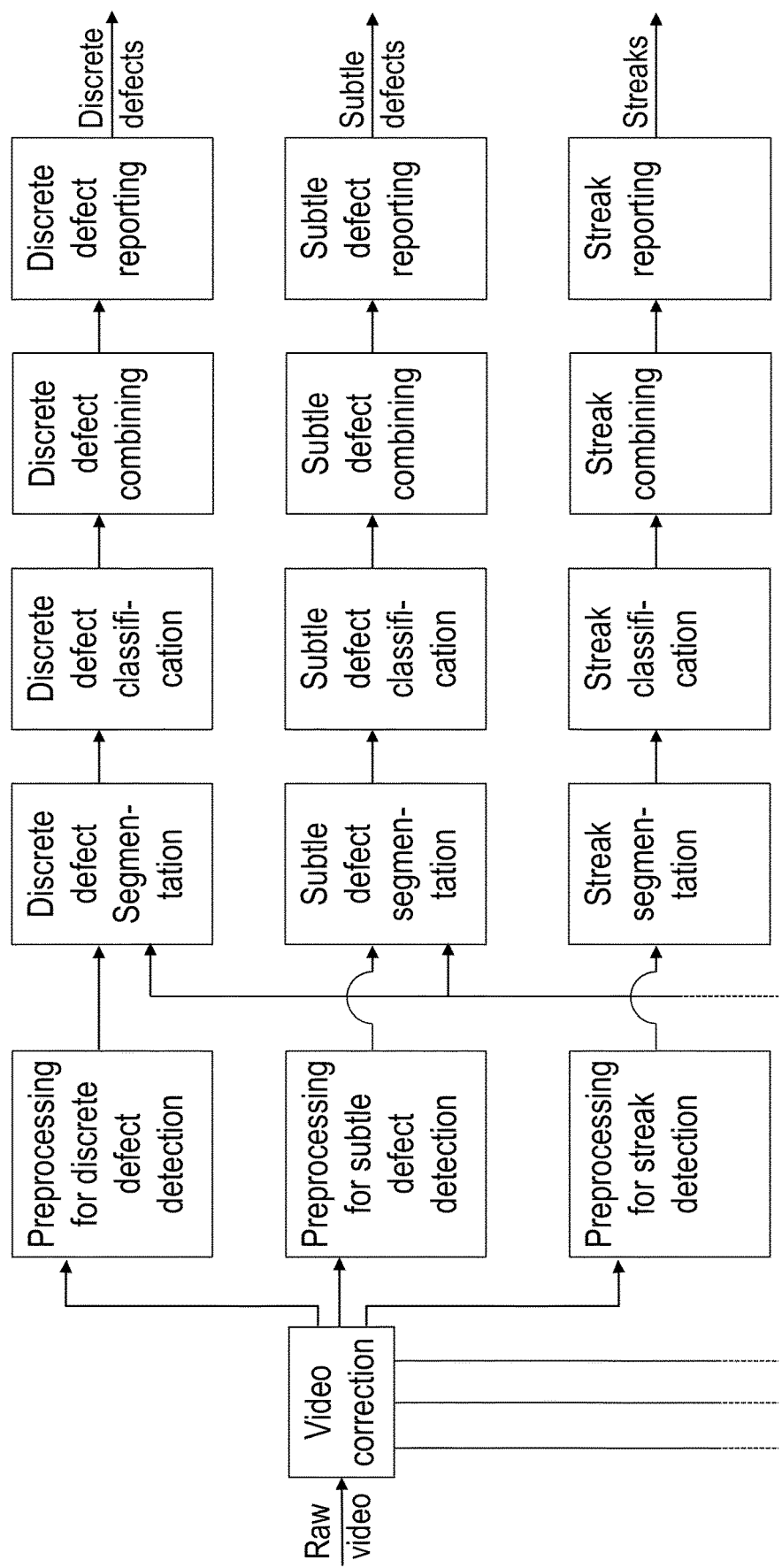
FIG. 3 shows an example of the parallel architecture of product imaging algorithms as implemented in the web inspection system of FIG. 1.
Figure 3:
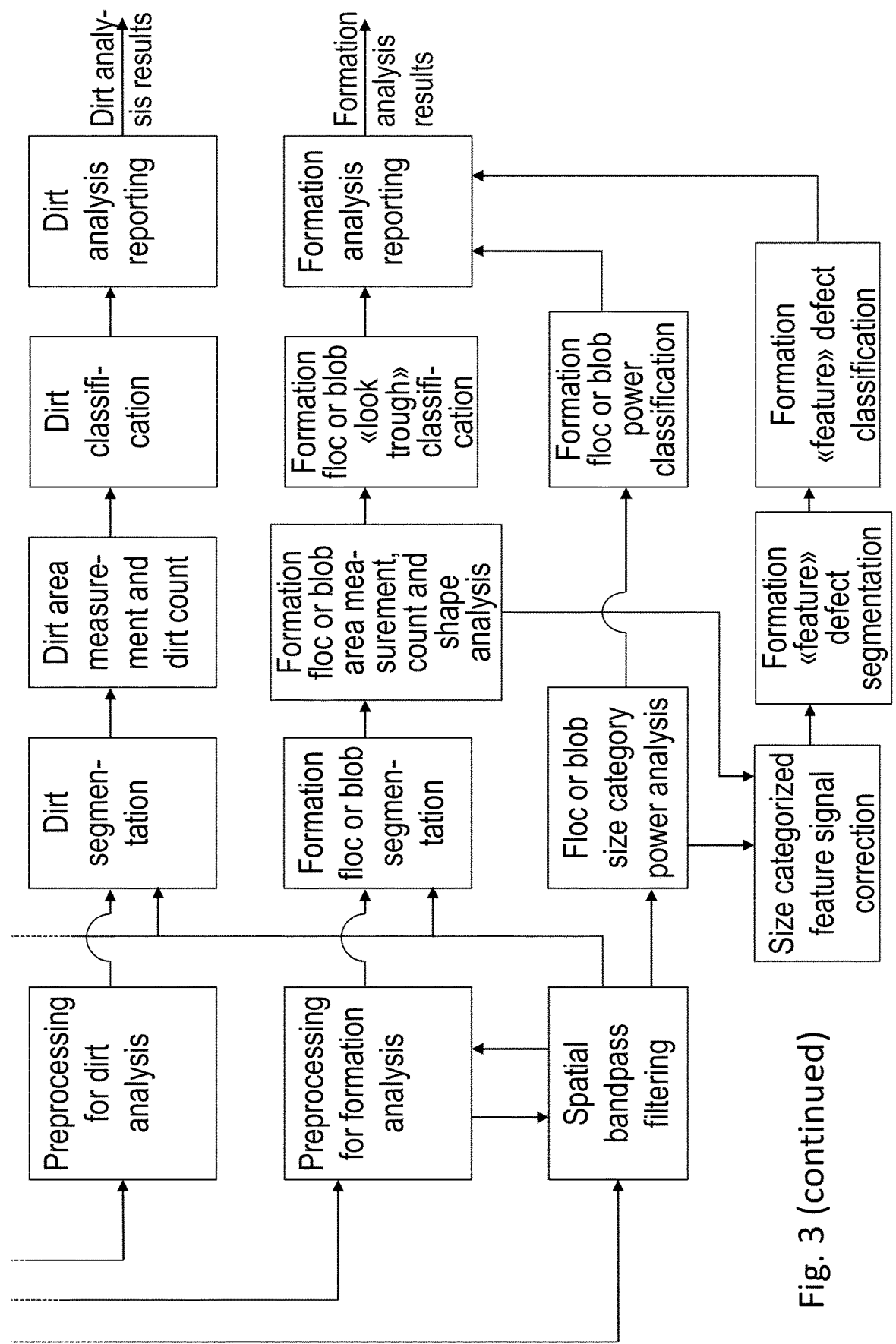

FIG. 3 shows an example of the parallel architecture of product imaging algorithms as implemented in the web inspection of FIG. 1, and illustrates how various inspection and monitoring methodologies, in particular for detection of discrete or strong defects, subtle or weak defects, streaks and/or dirt may interact with the formation analysis method in accordance with the present invention. In particular, as may be seen, various aspects of the invention as described herein may be combined with various aspects from the methods as described in EP patent application EP 16180281.4 or in WO 2017/198348 A1; or in Huotilainen, T., Laster, M., Riikonen, S., "Real-time ROI Morphometrics in High Quality Web Imaging", PaperCon, 2016, both of which are hereby included by reference in their entirety. In particular, the processed images $P_p$ with $p \in \{1; \ldots; P\}$ may be used starting point for these methods, allowing to also extract, e.g. shape and/or feature orientation information to be extracted for different size categories. Such information may then also be represented by means of local feature vectors and/or image feature vectors as described above, or combined with such feature vectors.

The method in accordance with the present invention is carried out on the image-processing unit 15. The results, in particular feature map and feature vectors obtained, may be displayed on a display contained in the operator station 16.

Figure 4:
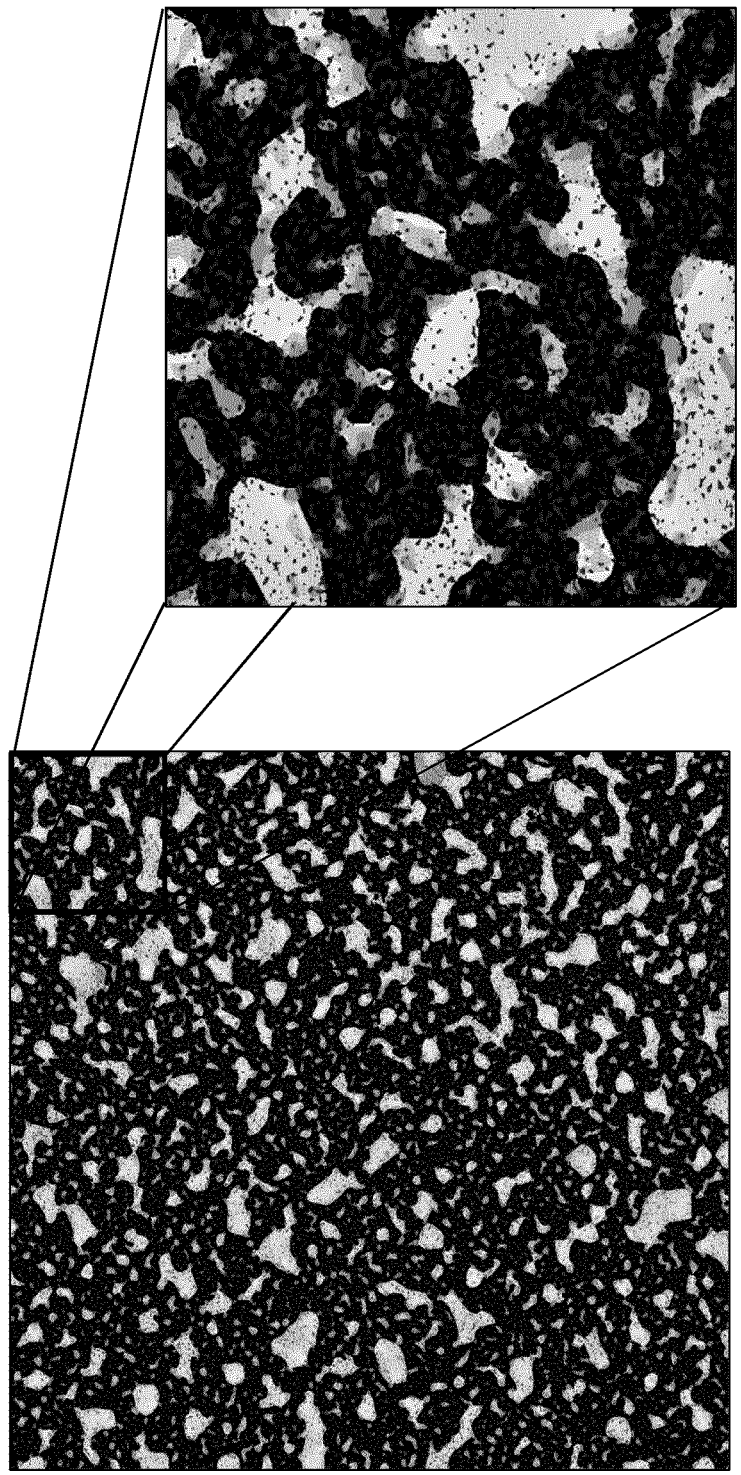
FIG. 4 shows bandpass filter bank based formation analysis result visualization and the corresponding bar graph.
Figure 4:
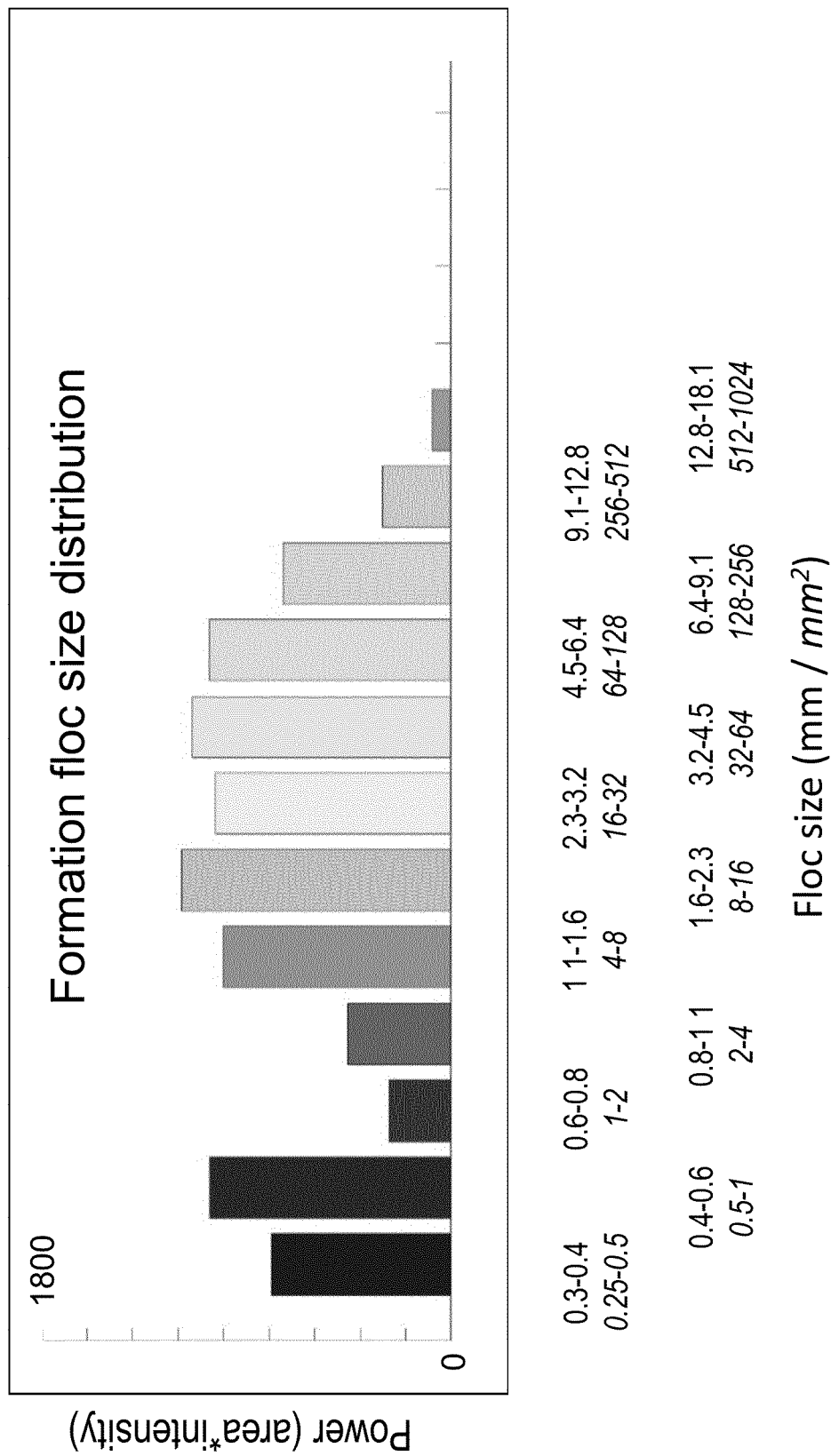

Bandpass filter bank based floc or blob detection results are visualized by combining 16 different floc or blob size categories, also referred to as floc or blob scales, in a feature map as illustrated in FIG. 4. Different colors are chosen and correspond to the floc or blob size categories. Additionally, the floc or blob power (unweighted area or area weighted by intensity) inside the size categories or scales are presented with a bar graph visualization of the respective image feature vector. The bar graph colors are the same as in the image representing the different size categories.

In an alternative and/or supplementary description, the method in accordance with the invention comprises the following steps:

1. A raw digital image (in particular a 12 bit image) of a product web is generated by a real-time linescan (or matrix) camera using fixed scan time, and said image is corrected by an adaptive flat line correction method developed for ABB WIS system earlier.

2. The method described in WO 2017/198348 A1, which is hereby included by reference in its entirety, and related to a real-time (online) full web paper formation analysis, or other product formation or surface analysis may optionally be utilized for "look through" type real-time analysis.

3. The corrected image is filtered with smoothing filter bank having smoothing filters, in particular spatial low pass filters, with different spatial widths.

4. The smoothed image signals are used to generate spatial bandpass filtered results by subtracting the low pass filtered images of the neighboring smoothing filters. This can be based on different kind of spatial low pass filters. Real-time streaming video imaging sets extremely high requirements for designing spatial filters. One option is to use Difference of Gaussians (DoG) filters but also other options seems to work. A combination of two directional CD Gaussian filtering (recursive Gaussian technique) and MD IIR filtering may also be use and provide results which are correlating with DoG method.

5. The bandpass filtered images are thresholded with a standard deviation (or a multiple thereof) of the original corrected image signal to form a base for floc power (area*intensity) analysis inside different size categories.

6. Online and/or offline image and bar graph based individual or combination visualization may be formed. An example of all scale combination visualization is shown in FIG. 4. The visualization is formed based on the different scale responses by selecting the scale (and thus the corresponding color) to individual pixels based on the local computed feature value of scales. Feature value, which is used to select the scale and defines to color, can be for example scale power, orientation or some other shape feature.

7. The results may be reported and visualized also in values if desired. The statistical analysis results are related to specified measurement area.

8. A system in accordance with the invention may be equipped with the detection of formation feature "defects" appearing in a specific floc size category (scale). This may be done by applying a gain correction principle to the feature distribution signal and forming a reference signal. Changes in the different formation size categories may then be detected. Feature vector may include power distribution, size categorized shape features, in particular orientation.

9. Additionally, automatically adjusted threshold values are generated and applied to the different scale bandpass filtered results to form binary images. The threshold levels are generated in light and dark sides of the dynamic range by autoadjustment to achieve desired percentage of exceeded floc and void areas of the product.

10. The detected floc and/or void region shapes are analyzed. The analysis of the floc and/or void areas is based on the real-time (online) digital filtering method, which combines the neighborhood pixels and calculates the features of the floc and/or void region simultaneously as described in WO 2017/198348 A1.

11. The area averages of the detected flocs and/or voids and the corresponding intensity averages of the same floc and/or void regions are calculated and combined.

12. The calculated floc and/or void features are stored and can be visualized in an online map.

Figure 5:
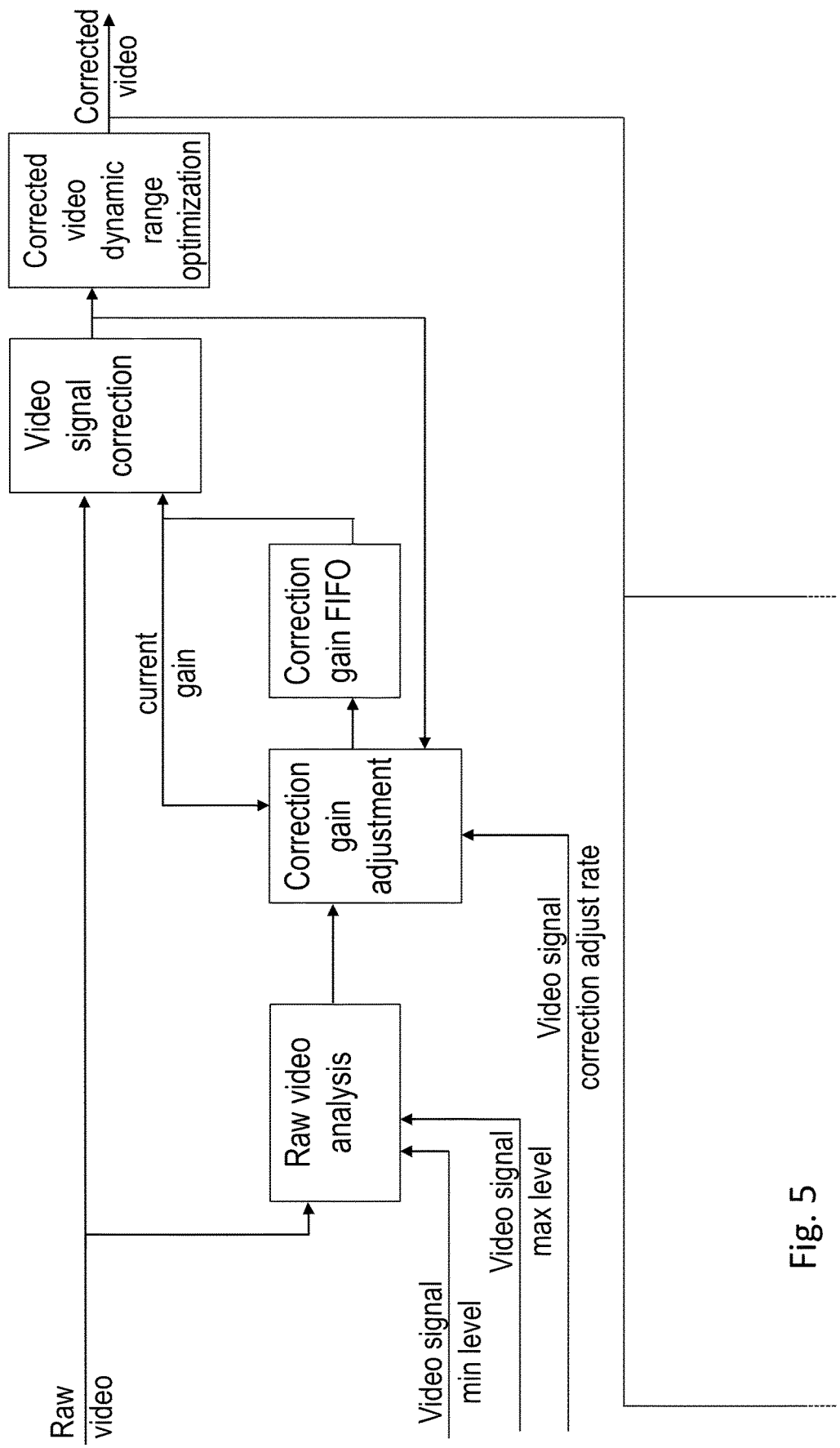
FIG. 5 shows a flow diagram of an exemplary embodiment of the method in accordance with the present invention.
Figure 5:
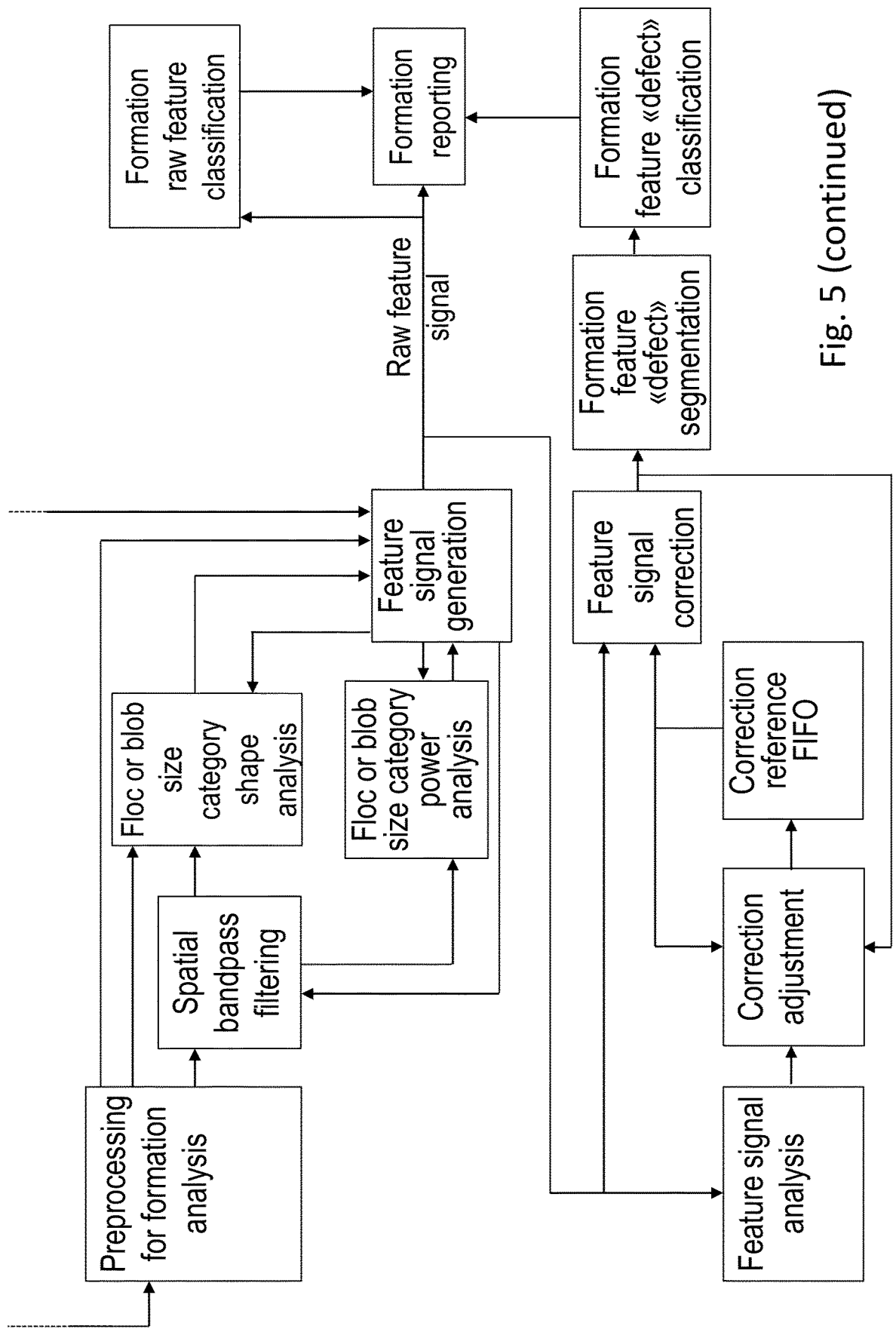

FIG. 5 shows a flow diagram which illustrates an exemplary embodiment of the method as described above.

Figure 6:
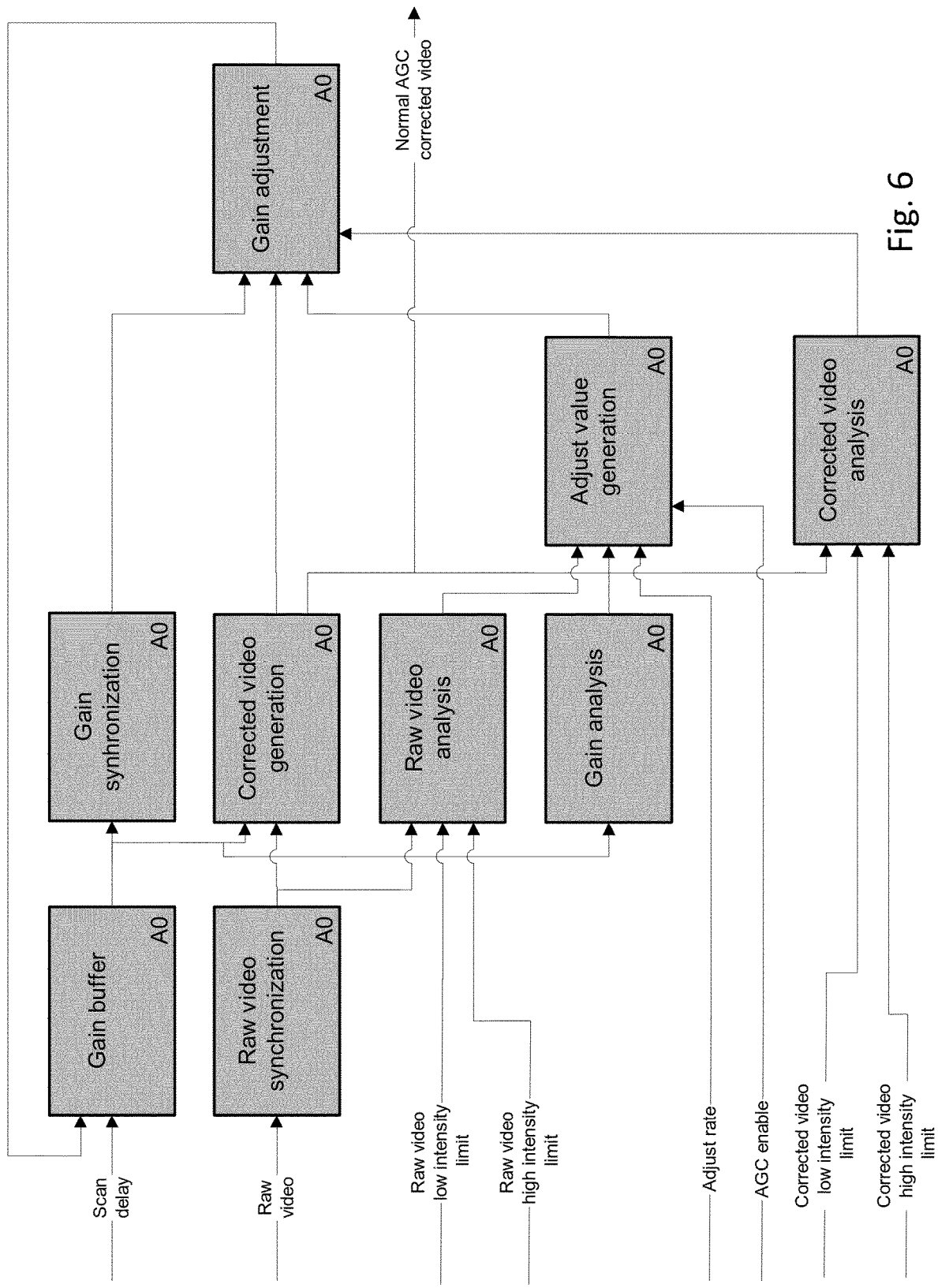
FIG. 6 shows a flow diagram of an exemplary internal structure of video correction.

The method starts (on the top left corner of FIG. 5) with raw video streamed from a line scan camera as described herein. The streamed video signal is then subjected an initial video signal correction as described herein, and exemplary shown in FIG. 6. The correction may in particular include corrections for effects due to imaging optics, in particular lenses, and illumination, in particular to ensure that response will be independent of illumination. Flat field correction may also be applied.

More specifically, in video correction method, a gain value may be stored in memory for every cross direction (CD) pixel position. Gain values g(n) may be adjusted regularly by a rate defined, e.g., by an operator. Thus, the corrected video signal nagc(n) is $$\mathrm{nagc}(n) = g(n)\mathrm{raw}(n) \qquad (1)$$

where g(n) is adjustable gain, raw(n) is raw video signal and n is the pixel position. In AGC the target for video level in long-term is in the middle of the whole dynamic range. If the corrected video signal nagc(n) is above the target, the gain value may be reduced. Correspondingly, if the signal value is below the target the gain value may be enlarged. Hence, the gain adjusting method may be expressed by $$g_{new}(n) = g_{old}(n) + \mathrm{sign}(t - \mathrm{nagc}(n))\mathrm{rate} \qquad (2)$$

where sign is a function which returns 1 for positive and −1 for negative results, rate defines the speed of adjusting (Normal AGC Adjust Rate control parameter) and t is the target value.

The signal as output from the initial video signal correction is fed back to a correction gain adjustment, which adjusts an instantaneous or current gain value applied by the initial video signal correction. For further processing, the signal as output from the initial video signal correction is subsequently subjected to corrected video dynamic range optimization, from which a corrected video signal is output, i.e. streamed.

The corrected video signal is then subjected to preprocessing for formation analysis, resulting in a preprocessed video signal. Preprocessing for formation analysis may include several preprocessing stages, which may be needed for the different filtering options and supporting the control of the formation analysis method; in particular:

a. small local area averaging (for example streaming average of 4 scan line pixels)

b. video scan line turning and synchronization for two directional lowpass infinite impulse response (IIR) filtering c. corrected video statistical and other measures for the parallel algorithm control and for feature vector/signal
  i. for example local area std, larger area std, skewness, kurtosis, CD average floc size based on direct algorithm, MD average floc size based on direct algorithm, anisotropy (CD average floc size/MD average floc size), floc orientation (average floc angle), void orientation (average void angle), floc size variation, void size variation, ii. automatic threshold level options generation based on statistical measures for the control of the parallel formation analysis method d. handling of the input signal validity: control of the measurement area, control of the valid intensity range, invalid product area elimination during the streaming formation analysis process i. measurement location control ii. input signal intensity analysis/control 1. for example discrete defect detection for formation analysis masking iii. masking (based on CD locations, or video intensity range)

1. for example formation method control/handling near camera viewing area edges or product edges iv. signal replacing or measurement enabling/disabling as needed.

The preprocessed video signal is then subjected to spatial bandpass filtering as described herein. The streamed signal obtained from the spatial bandpass filtering is then subjected to floc or blob size category power analysis as described herein, and feature signal generation, as described herein. In parallel to the floc or blob size category power analysis, floc or blob size category shape analysis as described in WO 2017/198348 A1 may also be carried out on the preprocessed video signal.

The corrected video signal, the preprocessed video signal and/or the results from the floc or blob size category shape analysis, may also be taken into account in the feature signal generation.

Further results from the feature signal generation may be fed back into the spatial bandpass filtering, in particular to adapt filter parameters as described herein, into floc or blob size category power analysis, and/or into floc or blob size category shape analysis.

Preprocessing for the formation analysis, spatial bandpass filtering, size category shape analysis, size category power analysis and feature signal generation are closely related and are working closely with each other during the streaming/parallel/feedback process and thus may be considered as one functional block, which is processing streaming corrected video input and giving feature signal (vector) as output.

A raw feature signal as delivered by the feature signal generation and described herein may then be used directly for formation reporting, in particular by creating a feature map as described herein, and displaying said feature map as described herein, and shown in the top part of FIG. 4. Formation reporting may also include results from formation raw feature classification, as described herein and shown exemplary in form of the bar graph in the bottom part of FIG. 4.

The raw feature signal may also be used as an input to feature signal analysis and/or feature signal correction.

Different approaches can be considered for the feature signal value correction i.e. the feature signal standard generation. We can use 1. different kinds of lowpass filtering methods including averaging, FIR or IIR based lowpass filtering.

In the simplest case we can use gain correction or offset value based correction for standard signal generation by calculating difference of the current corrected feature signal value and the corresponding target signal value. So in this case, there are gain and offset values stored in memory for every feature vector value to be corrected. Gain values g(n) and offset values a(n) can be adjusted regularly by operator defined rate. Thus, the corrected feature signal fea(v) is $$fea(v)=a(v)+g(v)rawfea(v) \quad (3)$$

where g(v) is adjustable gain, a(v) is adjustable offset value, rawfea(v) is raw feature signal and v is the feature value index. In feature signal correction the target for the vector value in long-term is in the desired position of the whole range. If the corrected feature signal value fea(v) is above the target the gain or offset value is reduced. Correspondingly, if the signal value is below the target the gain or offset value is enlarged. Hence, the adjusting methods can be expressed by $$g_{new}(v)=g_{old}(v)+\text{sign}(t(v)-fea(v))\text{grate} \quad (4)$$

$$a_{new}(v)=a_{old}(v)+\text{sign}(t(v)-fea(v))\text{arate} \quad (5)$$

where sign is a function which returns 1 for positive and −1 for negative results, grate and arate define the speed of adjusting and t(v) is the target value for the corresponding feature vector value. In normal cases only one adjustable correction principle is enabled at a time i.e. offset or gain correction and the other is either fixed or disabled. The chosen correction principle is depending on the basis and characteristics of the features of the feature vector. The adjustment process can be freezed after some time to keep the fixed reference or the adjustment can be slow continuous process.

The corrected feature signal represent the dissimilarity between standard (reference, which can for example represent normal quality or can represent a specific case, which we are searching) and current feature signals. The next step is to detect (feature defect segmentation) feature defects (large enough dissimilarities) by setting threshold levels to selected corrected feature vector values or for some feature vector value combination sets. Combination set value can be given by calculating the vector length of the feature vector value set utilizing chosen distance measure. The most common distance measure is Euclidean distance. Segmented feature vectors (selected/segmented by thresholding) can then be used for formation feature classification by utilizing chosen classification method. Examples of applicable classification methods are 1. decision trees, 2. k-NN (k-nearest neighbors) classifier, 3. neural network classifiers (for example MLP) and 4. simple matching classifier. In matching classifier the result can be derived by vector comparison between current feature vector and the class vectors in formation feature vector library.

In some special cases the formation quality can be analyzed based on straight classification of the raw feature signal.

Formation feature "defect" classification and formation feature "defect" segmentation may then be carried out on the corrected feature signal as described herein.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the term "comprising" does not exclude other elements or steps, and the indefinite article "a" or "an" does not exclude a plurality. The mere fact that certain features and/or measures are recited in different or separate embodiments, and/or mutually different dependent claims does not indicate that a combination of these features and/or measures may not be considered disclosed, claimed, or cannot be used to advantage. Any reference signs in the claims should not be construed as limiting the scope.

As used herein, i.e. anywhere in this document, the terms "computer," and related terms, e.g., "processor", "processing device," central processing unit (CPU)", "computing device," and "controller" may not be limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but is not limited to, a computer-readable medium, such as a random access memory (RAM), a computer-readable non-volatile medium, such as a flash memory. Alternatively, a floppy disk, a compact disc—read only memory (CD-ROM), a magneto-optical disk (MOD), a digital versatile disc (DVD), a USB stick and/or a flash memory card (e.g. CF, SD, miniSD, microSD) may also be used.

Further, as used herein, the terms "software" and "firmware" are interchangeable, and include any computer program which may be stored in memory for execution by computers as defined above, including workstations, clients, and/or servers.

As used herein, the term "non-transitory computer-readable media" is intended to be representative of any tangible computer-based device implemented in any method of technology for short-term and/or long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a computer as defined above, cause the computer to perform at least a portion of the methods described herein. Moreover, as used herein, the term "non-transitory computer-readable media" may include all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

As used herein, the term "real-time" may refer to at least one of the time of occurrence of an associated event, a time of measurement and collection of predetermined data, a time at which data is processed, and/or a time of a system response to the events and the environment. In the embodiments described herein, these activities and events may occur substantially instantaneously, and may in particular be scheduled to occur simultaneously, in particular within one clock cycle of an involved computer, or within a limited number, in particular less than 10, 50, 100, 500, 1000, or 10000 clock cycles, or less than 10n clock cycles with n<5, 6, 7, 8, or 9.

Unless stated otherwise, it shall be assumed throughout this entire document that a statement a≈b implies that $|a-b|/(|a|+|b|)<10^{-1}$, preferably $|a-b|/(|a|+|b|)<10^{-2}$, wherein a and b may represent arbitrary variables as described and/or defined anywhere in this document, or as otherwise known to a person skilled in the art. Further, a statement that a is at least approximately equal or at least approximately identical to b implies that a=b, preferably a=b. Further, unless stated otherwise, it shall be assumed throughout this entire document that a statement a>>b implies that a>10b, preferably a>100b; and statement a<<b implies that 10a<b, preferably 100a<b.

It should be noted that the term "comprising" does not exclude other features, in particular elements or steps, and that the indefinite article "a" or "an" does not exclude the plural. Also elements described in association with different embodiments may be combined. It should also be noted that reference signs in the claims shall not be construed as limiting the scope of the claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The disclosure as provided by this entire document also may include embodiments and variants with any combination of features, in particular individual features, mentioned or shown above or subsequently in separate or different embodiments, even if such features may only be shown and/or described in connection with further features. It may also include individual features from the figures, even if such features may only be shown in connection with further features, and/or are not mentioned in the above or following text. Likewise, any such features, in particular individual features, as described above, may also be excluded from the subject matter of the invention or from the disclosed embodiments and variants. The disclosure may include embodiments which include only the features described in the claims or in the exemplary embodiments, as well as embodiments which include additional other features.

Preferred embodiments of the present invention, in particular as described above, may be realized as detailed in the items listed below, advantageously in combination with one or more of the features as detailed above:

The invention claimed is:

1. A method, implemented on a computer, for detecting, monitoring and/or analyzing a quality of a product being produced in a manufacturing process, said product being transported, on a conveyor belt, in a moving direction during said manufacturing process, the method comprising the steps of:

a) acquiring an original image $P_0$ of the product, said image being representable as a two-dimensional digital image having a plurality of pixels having pixel values $P_{0,i,j}$ with $i \in \{1; \ldots; I\}$, $j \in \{1; \ldots; J\}$;

b) producing a plurality of P processed images $P_p$ with $p \in \{1; \ldots; P\}$, each of said processed images being representable by pixel values $P_{p,m,n}$ with $m \in \{1; \ldots; M\}$, $n \in \{1; \ldots; N\}$, said processed images being obtained by spatial filtering in form of spatial bandpass filtering, of the original image, wherein a different spatial filter in form of spatial bandpass filter, is used for obtaining each of the processed images, and c) combining at least two, preferably all, of the processed images $P_p$ with $p \in \{1; \ldots; P\}$ to obtain a feature map F being representable by values $F_{m',n'}$ with $m' \in \{1; \ldots; M'\}$, $n' \in \{1; \ldots; N'\}$, preferably $m' \in \{1; \ldots; M\}$, $n' \in \{1; \ldots; N\}$ wherein the values $F_{m',n'}$ of the feature map correspond to a predominant size category for m',n' with $F_{m',n'}=F(m',n') \triangleq p_{max,m',n'}$ with $P(p_{max,m',n'},m',n')>P(p,m',n')$ with $p \in \{1; \ldots; P\} \setminus \{p_{max,m',n'}\}$, wherein the processed images $P_p$ with $p\in\{1;\ldots;P\}$ are thresholded and converted to binary images representable by pixel values $P_{p,m,n}\in\{0;1\}$ for $p\in\{1;\ldots;P\}$, $m\in\{1;\ldots;M\}$, $n\in\{1;\ldots;N\}$.

2. The method according to claim 1, wherein the product is a web, in particular a paper web, and the quality being monitored and/or analyzed includes formation in said web.

3. The method according to claim 1, wherein the two-dimensional digital image by which the original image may be represented is provided as a stream of data, preferably in real time, and preferably without intermediate storage of the entire two-dimensional digital image.

4. The method according to claim 1, wherein at least one of the plurality of P processed images $P_p$ is provided as a stream of data, preferably in real time, and preferably without intermediate storage of said processed image.

5. The method according to claim 1, wherein characteristics of at least one spatial filter may be adapted, in particular by setting a filter parameter; and
 a) the pixel values $P_{p,m,n}$ are obtained successively by applying one or more of the filters successively to individual pixels or subsets of pixels representing the original image; wherein
 b) at least some pixel values $P_{p,m,n}$ that have already been obtained are used to adapt the characteristics of the at least one spatial filter prior to obtaining further pixel values.

6. The method according to claim 1, wherein the feature map $F_{m',n'}$ is obtained according to $F_{m',n'} \stackrel{def}{=} P_{max,m',n'}$ with $P_{max,m',n'} = \max\{P_{p,m',n'}|p\in\{1;\ldots;P\}\}$.

7. The method according to claim 6, wherein the feature map $F_{m',n'}$ is a scalar feature map, a first component of $F_{m',n'}$ contains values $P_{max,m',n'}$, while a second component contains values $P_{min,m',n'}$ with $P_{min,m',n'} = \min\{P_{p,m',n'}|p\in\{1;\ldots;P\}\}$.

8. The method according to claim 1, further comprising the step of:
 a) determining, from at least two, preferably all of the processed images $P_p$ with $p\in\{1;\ldots;P\}$, an image feature vector $v=(v_1,\ldots,v_P)$, wherein vector component $v_p$ of said image feature vector $v$ is determined from processed image $P_p$ with $p\in\{1;\ldots;P\}$.

9. The method according to claim 8, further comprising determining the image feature vector $v$ on the basis of the feature map F.

10. The method according to claim 8, further comprising determining a first global image feature vector $v$ on the basis of the whole original image and a second local image feature vector on the basis of a subregion or subarea of the original image and comparing the first and second image feature vectors.

11. The method according to claim 8, further comprising the step of applying gain and/or offset correction to at least a selection of processed images $P_p$ with $p\in\{1;\ldots;P\}$, in particular applying individual gain and/or offset correction to a selection of processed images $P_p$ with $p\in S\subset\{1;\ldots;P\}$, wherein gain correction and/or offset for processed images $P_p$ is repeatedly updated based on a deviation between a current value of a local or image feature vector component $v_p$ and a target value $\hat{v}_p$ for said feature vector component $v_p$.

12. The method according to claim 1, wherein
 a) the two-dimensional original image is obtained from a raw digital image of product web, preferably obtained by means of a real-time linescan or matrix camera using fixed scan time, and
 b) said raw digital image is corrected by an adaptive flat line correction method.

13. The method according to claim 1, wherein
 a) in step b) of claim 1, a plurality of smoothed images $B_q$ with $q\in\{1;\ldots;Q\}$ each of said smoothed images being representable by pixel values $B_{q,m,n}$, with $m\in\{1;\ldots;M\}$, $n\in\{1;\ldots;N\}$, is produced, each of said smoothed images being obtained applying a spatial low pass or smoothing filter to the original image, with a different filter being used for each of the smoothed images $B_{q,m,n}$;
 b) each of the processed images $P_p$ with $p\in\{1;\ldots;P\}$ is produced by subtracting two smoothed images $B_{p1,m,n}$, $B_{p2,m,n}$ with $p1\neq p2$.

14. The method according to claim 1, wherein
 a) a standard deviation $\sigma$ of the original image $P_0$ is determined;
 b) the processed images $P_p$ with $p\in\{1;\ldots;P\}$ are thresholded with the standard deviation $\sigma$ or a multiple thereof.

15. The method according to claim 14, further characterized in that the feature map F is displayed as a two-dimensional digital color image, with a different color being displayed for each different value of $F_{m',n'}$ with $m\in\{1;\ldots;M'\}$, $n\in\{1;\ldots;N'\}$.

16. The method according to claim 1, further comprising the step of displaying the feature map F as a two-dimensional digital image.

17. The method according to claim 1, wherein at least one bandpass filter is a two-dimensional bandpass filter having transfer characteristics for a first spatial direction which are different from transfer characteristics for a second spatial direction.

18. An optical web inspection system comprising:
 a) an image acquisition unit for acquiring a raw image and/or an original image $P_0$ of a web being transported in a moving direction during a web manufacturing process,
 b) a digitization unit, preferably included by the image acquisition unit, for determining pixel values $P_{0,i,j}$ with $i\in\{1;\ldots;I\}$, $j\in\{1;\ldots;J\}$ representing said original image $P_0$,
 c) a processing unit configured to execute the method including the steps:
  a) acquiring an original image $P_0$ of the product, said image being representable as a two-dimensional digital image having a plurality of pixels having pixel values $P_{0,i,j}$ with $i\in\{1;\ldots;I\}$, $j\in\{1;\ldots;J\}$;
  b) producing a plurality of P processed images $P_p$ with $p\in\{1;\ldots;P\}$, each of said processed images being representable by pixel values $P_{p,m,n}$ with $m\in\{1;\ldots;M\}$, $n\in\{1;\ldots;N\}$, said processed images being obtained by spatial filtering in form of spatial bandpass filtering, of the original image, wherein a different spatial filter in form of spatial bandpass filter, is used for obtaining each of the processed images, and
  c) combing at least two, preferably all, of the processed images $P_p$ with $p\in\{1;\ldots;P\}$ to obtain a feature map F being representable by values $F_{m',m'}$ with $m'\in\{1;\ldots;M'\}$, $n'\in\{1;\ldots;N'\}$, preferably $m'\in\{1;\ldots;M\}$, $n'\in\{1;\ldots;N\}$ wherein the values $F_{m',n'}$ of the feature map correspond to a predominant size category for m', n' with $F_{m',n'}=F(m',n')\stackrel{def}{=}p_{max,\ m',n'}$ with $P(p_{max,m',n'},m',n')>P(p,m',n')$ with $p\in\{1;\ldots;P\}\setminus\{p_{max,m',n'}\}$, wherein the processed images $P_p$ with $p\in\{1;\ldots;P\}$ are thresholded and converted to binary images representable by pixel values $P_{p,m,n} \in \{0; 1\}$ for $p \in \{1; \ldots; P\}$, $m \in \{1; \ldots; M\}$, $n \in \{1; \ldots; N\}$; and d) a display unit for displaying results obtained when executing said method, in particular the feature map $F_{m',n'}$ and/or an image feature vector v.

19. The optical web inspection system according to claim 18, wherein the processing unit includes a field-programmable gate array.

\* \* \* \* \*